(12) United States Patent
Sternby

(10) Patent No.: US 6,258,027 B1
(45) Date of Patent: Jul. 10, 2001

(54) METHOD AND DEVICE FOR CALCULATING DIALYSIS EFFICIENCY

(75) Inventor: Jan Sternby, Lund (SE)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/424,900

(22) PCT Filed: Jun. 2, 1998

(86) PCT No.: PCT/SE98/01048

§ 371 Date: Nov. 30, 1999

§ 102(e) Date: Nov. 30, 1999

(87) PCT Pub. No.: WO98/55166

PCT Pub. Date: Dec. 10, 1998

(30) Foreign Application Priority Data

Jun. 2, 1997 (SE) .................................................... 9702074
Dec. 9, 1997 (FR) .................................................... 97 15818

(51) Int. Cl.⁷ ........................................................ A61B 5/00
(52) U.S. Cl. ........................... 600/366; 600/573; 210/646
(58) Field of Search .................................... 600/309, 366, 600/573, 584; 210/634, 600, 645–646

(56) References Cited

U.S. PATENT DOCUMENTS

| 4,324,663 | 4/1982 | Hirel et al. . |
|---|---|---|
| 5,598,841 | 2/1997 | Taniji et al. . |
| 5,644,240 | 7/1997 | Brugger . |

FOREIGN PATENT DOCUMENTS

| 2178430 | 12/1996 | (CA) . |
|---|---|---|
| 0 547 025 A1 | 6/1993 | (EP) . |
| 0 920 877 A1 | 6/1999 | (EP) . |
| WO 94/08641 | 4/1994 | (WO) . |

*Primary Examiner*—Angela D. Sykes
*Assistant Examiner*—Ryan Carter
(74) *Attorney, Agent, or Firm*—Lerner, David, Littenberg, Krumholz & Mentlik, LLP

(57) ABSTRACT

Methods and apparatus for calculating a parameter of mass exchange of a solute fluid are disclosed including passing the solute in a predetermined volume of the fluid on one side of a semi-permeable membrane in a dialyzer, passing an exchange fluid on the other side of the semi-permeable membrane, obtaining a concentration curve by repeatedly measuring the concentration of a solute such as urea in the mass exchange fluid, fitting an approximate curve having a logarithm comprising a substantially straight line with at least a portion of a concentration curve, determining a parameter of the approximation curve, and calculating the mass of urea in the predetermined volume of fluid by the formula $m=(Q_d \times c_d)/P$ where P is the mass of the urea, $Q_d$ is the flow rate of the exchange fluid, $C_d$ is the concentration of the urea in the exchange fluid, and P is the parameter.

49 Claims, 5 Drawing Sheets

METHOD AND DEVICE FOR CALCULATING DIALYSIS EFFICIENCY

FIELD OF THE INVENTION

The present invention relates to a method and apparatus for calculating dialysis efficiency using values obtained from a urea sensor for the calculations. The calculations can also predict certain conditions which may require intervention.

BACKGROUND OF THE INVENTION

In hemodialysis it is common to dialyse a patient three times per week, with time periods of three to four hours per treatment. The object of this treatment is to provide an adequate dose of dialysis to the patient. Such a dose of treatment can be defined in different ways.

One commonly used definition uses the urea molecule as a marker molecule and prescribes that the dialysis clearance (K) divided by the distribution volume (V) of urea times total treatment time (t) should exceed a certain constant, for example Kt/V is greater than one per treatment. The weekly dialysis dose is then Kt/V greater than three.

One common way of measuring Kt/V is by measuring the concentration of urea ($c_b$) in the plasma before and after the treatment. The ratio $R=c_{bpost}/c_{bpre}$ is correlated to Kt/V. A number of different equations have been suggested for the calculation of Kt/V, such as:

$$Kt/V = -\ln(R-0.03) + (4-3.5 \cdot R) \cdot UF/W \quad (1)$$

where UF=ultrafiltration volume removed in liters and W=post-dialysis weight in kg.

Several clinical studies have been performed evaluating Kt/V in which post-dialysis plasma urea ($c_{bpost}$) has been measured immediately after the dialysis, usually less than two minutes after ending the treatment. However, most patients have a rebound of $c_{bpost}$. If an equilibrated post-treatment ($c_{bpost}$) is measured after about 30 minutes, for example, a more "true" Kt/V can be measured.

The measurement of $c_b$ is not unproblematic. It is required that a blood sample be taken before and after the dialysis treatment. Such samples are then analysed by the hospital's laboratory. The resulting values are thus provided with a substantial time delay. In this way it is not possible to adjust the actual treatment so that a prescribed dose is obtained.

The post-treatment sample must be taken with care, especially regarding timing, to avoid false values due to cardiopulmonary or access recirculation. Another source of error is the rebound mentioned above.

If an equilibrated post-treatment sample should be taken, such sample should be taken about 30 to 60 minutes after terminating the treatment, which is not practical for the patient. The amount of rebound and the rate of rebound varies considerably from patient to patient.

These problems have been addressed in the prior art in different manners.

International Application No. WO 94/08641 describes the use of a urea monitor for assessing the adequacy of an dialysis treatment. The urea monitor is connected to the dialysis effluent line and measures the concentration of urea in the dialysate leaving the dialyzer.

According to this specification, it is necessary to know or measure the pre-dialysis plasma urea value ($c_{bpre}$). Such measurements can be made by measuring the urea concentration in an equilibrated sample taken before initiation of the treatment. However, such initial measurement takes time and the dialysis machine needs to be specially constructed to obtain such pre-dialysis urea value.

Other indicators of adequate dialysis are URR and SRI:

$$URR = 1-R = 1-c_{b\,post}/c_{b\,pre} \quad (2)$$

$$SRI = (m_{urea\,pre} - m_{urea\,post})/m_{urea\,pre} \quad (3)$$

where $m_{urea\,pre}$ and $m_{urea\,post}$ are pre and post amounts of urea in the body, respectively.

The object of the present invention is to provide a method and apparatus for determining the efficiency of a dialysis treatment and monitoring delivered dose of treatment on-line.

Another object of the present invention is to provide a method and apparatus for continuously monitoring the dialysis efficiency for adjusting the dialysis treatment on line when required, for example if the dialyzer is clotted.

A further object of the present invention is to provide a method and apparatus for estimating the dose of dialysis delivered without the need for taking blood samples or requiring the dialysis machine to make any special adjustments such as taking an equilibrated pre-dialysis plasma urea concentration.

SUMMARY OF THE INVENTION

In accordance with the present invention, these and other objects have now been realized by the invention of method for calculating a parameter of the mass exchange of a solute in a fluid comprising:

passing the solute in a predetermined volume of the fluid on one side of a semi-permeable membrane in a mass exchange device, passing an exchange fluid on the other side of the semi-permeable membrane, obtaining a solute concentration curve by repeatedly measuring the concentration of the solute in the exchange fluid, fitting an approximation curve having a logarithm comprising a substantially straight line with at least a portion of the concentration curve, determining a parameter of the approximation curve, and calculating the mass of the solute in the predetermined volume of the fluid by the formula $m=Q_d \cdot c_d/P$ wherein m comprises the mass of the solute, $Q_d$ comprises the flow rate of the exchange of fluid, $c_d$ comprises the concentration of the solute in the exchange fluid, and P comprises the parameter.

In a preferred embodiment, the method includes determining the flow rate of the exchange fluid, integrating the product of the flow rate of the exchange fluid and the concentration of the solute in the exchange fluid over time in order to calculate the accumulated mass of the solute in the exchange fluid, and calculating a solute reduction index by the formula:

$$SRI = (U-G \cdot t)/(m+U-G \cdot t)$$

wherein

SRI comprises the solute reduction index,

U comprises the accumulated mass of the solute in the exchange fluid,

G comprises the production of the solute over time, and t comprises time.

In accordance with one embodiment of the method of the present invention, the mass exchange device comprises a dialyzer, the mass exchange fluid comprises a dialysate fluid, and the solute comprises urea.

In accordance with another embodiment of the method of the present invention, the parameter corresponds to a whole body clearance divided by the predetermined volume of the fluid.

In accordance with another embodiment of the method of the present invention, the passing of the exchange fluid on the other side of the semi-permeable membrane comprises passing a finite initial concentration of the solute and wherein the measuring of the solute concentration comprises repeatedly measuring the difference of the solute concentration across the semi-permeable membrane.

In accordance with another embodiment of the method of the present invention, the fitting of the approximating curve comprises obtaining a compensated concentration by subtracting a predetermined concentration term from the concentration of the solute, obtaining the logarithm of the compensated concentration, and fitting a straight line to the logarithm of the compensated concentration, whereby the predetermined concentration term compensates for the generation of the solute.

In accordance with another embodiment of the method of the present invention, the parameter of the approximation curve comprises a slope of the substantially straight line.

In accordance with another embodiment of the method of the present invention, the fitting of the approximation curve excludes a predetermined initiation period. Preferably, the predetermined initiation period comprises about 60 minutes.

In accordance with another embodiment of the method of the present invention, the method includes periodically interrupting the passing of the exchange fluid on the other side of the semi-permeable membrane for a first time period, and adjusting the time scale by replacing the first time period with a second time period, the second time period being less than the first time period.

In accordance with another embodiment of the method of the present invention, the parameter comprises a slope with respect to time in the following equation:

$$\ln(c_d - G/Q_d) = \ln(c_0 - G/Q_d) - Kt/V \qquad (I)$$

wherein $c_d$ comprises the concentration of the solute in the exchange fluid,

G comprises the production of the solute over time, $c_0$ comprises the concentration of the solute in the exchange fluid at time zero, K/V comprises the relative whole body dialysis efficiency, and t comprises the time from time zero.

In a preferred embodiment, the method includes determining the momentary mass by the equation:

$$m_1 = (Q_d \cdot c_{d1})/(K/V)_1$$

wherein $(K/V)_1$ is determined in accordance with equation (I), and including determining the momentary relative efficiency at a predetermined time by the equation:

$$(K/V)_2 = (Q_d \cdot c_{d2})/m_2$$

wherein $(K/V)_2$ comprises the momentary relative efficiency, $m_2$ comprises $m_1 - (U_2 - U_1) + G(t_2 - t_1)$, $c_{d1}$ comprises the concentration of the solute in the exchange fluid at time $t_1$, $c_{d2}$ comprises the concentration of solute in the exchange fluid at time $t_2$, $U_1$ comprises the accumulated mass of the solute in the exchange fluid at time $t_1$, and $U_2$ comprises the accumulated mass of the solute in the fluid at time $t_2$. In a preferred embodiment, the method includes integrating the relative dialysis efficiency over time, whereby an estimate of the total dialysis dosage can be obtained.

In accordance with another embodiment of the method of the present invention, the fitting of the approximation curve comprises calculating a line passing through the greatest number of points in the logarithm of the concentration curve. Preferably, the calculating is compensated.

In accordance with another embodiment of the method of the present invention, the method includes calculating the momentary mass from all values of the concentration of the solute in the exchange fluid from the substantially straight line within a predetermined time period, calculating a calculated initial mass from the momentary mass, and estimating the actual initial mass from the calculated initial mass. Preferably, estimating of the actual mass comprises determining the mean or median value of the calculated initial mass.

In accordance with another embodiment of the method of the present invention, the method includes determining the momentary mass of the solute in the exchange fluid by determining the actual concentration of the solute in the exchange fluid by a method selected from the group consisting of analyzing a blood sample and equilibrating the exchange fluid with blood and determining the distribution value of the solute.

In accordance with another embodiment of the method of the present invention, the method includes estimating the distribution volume of the fluid, and determining the concentration of the solute in the fluid by dividing the calculated mass by the distribution volume. Preferably, estimating of the distribution volume is carried out utilizing Watson's formula.

In accordance with another embodiment of the method of the present invention, the method includes measuring the concentration of the solute in the fluid and determining the distribution volume of the solute in the fluid by dividing the calculated mass and the concentration of the solute in the fluid.

In accordance with another embodiment of the method of the present invention, the method includes introducing a disturbance into the dialyzer and measuring the resulting effect in the dialysate, whereby the concentration of the solute in the fluid is measured, calculating the effective clearance of the dialyzer from the measured resulting effect on the dialysate, calculating the plasma water concentration of the solute utilizing the formula $$c_{pw} = Q_d \cdot c_d / K_e$$

wherein $c_{pw}$ comprises the plasma water concentration of urea upon initiation of the dialysis, $Q_d$ comprises the effluent dialysate flow rate from the dialyzer, $c_d$ comprises the concentration of urea extrapolated to initiation of the dialysis, and $K_e$ comprises the effective clearance of the dialyzer for urea; and determining the distribution volume of the urea in the fluid by means of the formula:

$$V = m_0 / c_{pw}$$

wherein $m_0$ comprises the initial mass.

In accordance with another embodiment of the method of the present invention, the method includes determining a deviation of the concentration curve from the approximation curve, and emitting an alarm based upon the deviation with respect to a predetermined threshold level.

In accordance with another embodiment of the method of the present invention, the parameter comprises the slope of $\ln(c_d-c_k)$ as a function of $(V_0/UF)\ln(V/V_0)$ in the equation:

$$\ln(c_d-c_k)=\ln(c_0-c_k)+[(K-UF)/V_0]\cdot[(V_0/UF)\ln(V/V_0)] \quad \text{(II)}$$

wherein $c_d$ comprises the concentration of the dialysate at time t, $c_0$ comprises the concentration of the dialysate at time zero, $c_k$ comprises $G/[Q_d(1-UF/K)]$, G comprises the generation of the solute, $Q_d$ comprises the flow rate of the dialysate, K comprises the whole body clearance, $V_0$ comprises the distribution volume prior to treatment, UF comprises the ultrafiltration per unit time, and $[(K-UF)/V_0]$ comprises the slope.

Preferably, the method includes determining the momentary mass according to the equation:

$$m_1=(Q_d\cdot c_{d1})/(K/V)_1$$

wherein $(K/V)_1=(K/V_0)/(1-t_1\cdot UF/V_0)$ and $(K/V_0)$ is determined according to equation (V) and including estimating $UF/V_0$, wherein the momentary relative efficiency at a given time is determined according to the equation:

$$(K/V)_2=(Q_d\cdot c_{d2})/m_2$$

wherein $$m_2=m_1-(U_2-U_1)+G(t_2-t_1)$$

and $c_{d1}$ comprises the concentration of the dialysate at time $t_1$, $c_{d2}$ comprises the concentration of the dialysate at time $t_2$, $U_1$ comprises the accumulated mass of the solute at time $t_1$, and $U_2$ comprises accumulated mass of the solute at time $t_2$.

In accordance with the present invention, apparatus has also been provided for calculating a parameter of a mass exchange procedure comprising:

mass exchange means for passing a solute in a predetermined volume of a fluid on one side of a semi-permeable membrane and passing a mass exchange fluid on the other side of the semi-permeable membrane in order to exchange the mass of the solute therebetween;

measuring means for measuring the concentration of the solute in the mass exchange fluid, whereby a solute concentration curve can be provided;

first calculation means for fitting an approximation curve having a logarithm comprising a substantially straight line to at least a portion of the solute concentration curve;

second calculation means for determining a parameter of the approximation curve; and third calculation means for calculating the mass of the solute in the predetermined volume of the fluid by means of the formula $$m=(Q_d\cdot c_d)/P$$

wherein m comprises the mass of solute in the predetermined volume of the fluid, $c_d$ comprises the concentration of the solute in the mass exchange fluid, P comprises the parameter, and $Q_d$ comprises the flow rate of the mass exchange fluid.

In accordance with another embodiment of the apparatus of the present invention, the apparatus includes flow rate determination means for determining the flow rate of the mass exchange fluid, fourth calculation means for calculating the accumulated mass of the solute in the mass exchange fluid from the mass exchange flow rate and the concentration of the solute by integrating the product of the mass exchange flow rate and the solute concentration in the mass exchange fluid over time, and fifth calculation means for calculating a solute reduction index according to the formula:

$$SRI=(U-G\cdot t)/(m+U-G\cdot t)$$

wherein

SRI comprises the solute reduction index,

G comprises the production of the solute over time, and t comprises time.

In accordance with another embodiment of the apparatus of the present invention, the mass exchange means comprises a dialyzer, the exchanging of the solute between the sides of the semi-permeable membrane comprises dialysis, the mass exchange fluid comprises a dialysate fluid, and the solute comprises urea. In accordance with a preferred embodiment, the apparatus includes flow rate measuring means for measuring the flow rate of the dialysate, and wherein the third calculation means includes means for calculating the accumulated mass of the urea in the dialysate by integrating the product of the flow rate of the dialysate and the concentration of the solute in the dialysate fluid over time.

In accordance with another embodiment of the apparatus of the present invention, the dialysate fluid has an initial concentration of the urea which is greater than zero, and wherein the measuring means measures the concentration difference across the semi-permeable membrane.

In accordance with another embodiment of the apparatus of the present invention, the first calculation means includes means for subtracting a first compensation term comprising $G/Q_d$ from the concentration of the urea in order to obtain a compensated concentration, whereby a straight line can be fitted to the logarithm of the compensated concentration so that the compensation term compensates for the production of the urea over time.

In accordance with another embodiment of the apparatus of the present invention, the parameter comprises the slope of the substantially straight line.

In accordance with another embodiment of the apparatus of the present invention, the first calculation means includes means for excluding data obtained during the initiation period. Preferably, the initiation period comprises about 60 minutes.

In accordance with another embodiment of the apparatus of the present invention, the first calculation means includes means for adjusting the time scale whereby when the flow of the dialysate fluid is interrupted for a first time period the first time period can be replaced with a second time period, the second time period being shorter than the first time period.

In accordance with another embodiment of the apparatus of the present invention, the parameter comprises the slope with respect to time, and wherein the second calculation means includes means for calculating the parameter by means of the following equation:

$$\ln(c_d - G/Q_d) = \ln(c_0 - G/Q_d) - Kt/V \qquad (I)$$

wherein $c_d$ comprises the concentration of the dialysate at time t,

G comprises the generation of the urea, $Q_d$ comprises the flow of the dialysate fluid, $c_0$ comprises the concentration of the dialysate fluid at time zero, K/V comprises the relative dialysis efficiency, and t comprises the time from time zero.

In accordance with another embodiment of the apparatus of the present invention, the second calculation means includes means for calculating a momentary mass according to the equation:

$$m_1 = (Q_d \cdot c_{d1})/(K/V)_1$$

wherein $m_1$ comprises the momentary mass, $(K/V)_1$ is determined according to equation (I), and the momentary relative efficiency at any time is determined according to the equation:

$$(K/V)_2 = (Q_d \cdot c_{d2})/m_2$$

wherein $(K/V)_2$ comprises the momentary relative efficiency, $$m_2 = m_1 - (U_2 - U_1) + G(t_2 - t_1),$$

$c_{d1}$ comprises the concentration of the dialysate fluid at time $t_1$, $c_{d2}$ comprises the concentration of the dialysate fluid at time $t_2$, $U_1$ comprises the accumulated mass of the dialysate fluid at time $t_1$, and $U_2$ comprises the accumulated mass of dialysate fluid at time $t_2$.

Preferably, the second calculation means comprises means for integrating the relative dialysis efficiency over time whereby an estimate of the total dialysis dose is provided.

In accordance with another embodiment of the apparatus of the present invention, the second calculation means comprises means for fitting the approximation curve by calculating a line passing through the greatest number of points in the logarithm of the concentration curve. Preferably, the calculation means includes means for calculating the momentary mass of the solute using the values of the concentration of the solute in the mass exchange fluid within a predetermined limit from the substantially straight line which can then be used to calculate the initial mass of the solute, which can be used to estimate the actual initial mass of the solute.

In accordance with another embodiment of the apparatus of the present invention, the second calculation means further includes means for estimating the actual initial mass based upon the median or mean value of the initial mass.

In accordance with another embodiment of the apparatus of the present invention, the apparatus includes means for determining a momentary mass of the solute by analyzing a blood sample or by equilibration of the dialysate with blood and determining the actual concentration of the solute and measuring the distribution volume of the solute.

In accordance with another embodiment of the apparatus of the present invention, the apparatus includes means for estimating the distribution volume of the dialysate and for determining the concentration of the urea in the dialysate by dividing the calculated mass by the volume. Preferably, the means for estimating the distribution volume utilizes Watson's formula.

In accordance with another embodiment of the apparatus of the present invention, the apparatus includes means for measuring the concentration of the urea in the dialysate and for determining the distribution volume by dividing the calculated mass by the concentration.

In accordance with another embodiment of the apparatus of the present invention, the measuring means comprises means for introducing a disturbance into the dialyzer, means for measuring the resulting effect in the dialysate and for calculating the effective clearance of the dialyzer from the resulting measurements, means for calculating the plasma water concentration of the solute by the formula:

$$c_{pw} = Q_d \cdot c_d / K_e$$

wherein $c_{pw}$ comprises the plasma water concentration of urea at the initiation of the dialysis, $Q_d$ comprises the flow rate of the dialysate, $c_d$ comprises the concentration of the urea extrapolated to the initiation of the dialysis procedure, $K_e$ comprises the effective clearance of the dialyzer for urea, and including means for determining the distribution volume V of the urea using the formula $V = m_0/c_{pw}$ where V comprises the distribution volume.

In accordance with another embodiment of the apparatus of the present invention, the apparatus includes means for determining a deviation of the concentration curve from the approximation curve and alarm means for emitting an alarm upon deviation greater than a predetermined threshold level.

In accordance with another embodiment of the apparatus of the present invention, the parameter comprises a slope and wherein the second calculation means comprises means for calculating the slope in the equation:

$$\ln(c_d - c_k) = \ln(c_0 - c_k) + [(K - UF)/V_0][(V_0/UF)\ln(V/V_0)] \qquad (II)$$

wherein $[(K-UF)/V_0]$ comprises the slope of a predetermined line, $\ln(c_d - c_k)$ comprises the line, $c_d$ comprises the concentration of the dialysate at time t, $c_k$ comprises $G/[Q_d(1-UF/K)]$, G comprises the generation of the urea, $Q_d$ comprises the flow of the dialysate, $c_0$ comprises a concentration of the dialysate at time zero, K/V comprises the relative dialysis efficiency, and UF comprises the ultrafiltration over time.

In accordance with another embodiment of the apparatus of the present invention, the second calculation means includes means for calculating a momentary mass according to the equation:

$$m_1 = (Q_d \cdot c_{d1})/(K/V)_1$$

wherein $$(K/V)_1 = (K/V_0)/(1 - t_1 \cdot UF/V_0),$$

$(K/V_0)$ is determined according to equation (V) and $UF/V_0$ is estimated, and the momentary relative efficiency at any given predetermined time is determined according to the equation:

$$(K/V)_2 = (Q_d \cdot c_{d2})/m_2$$

where $(K/V)_2$ comprises the momentary relative efficiency, $$m_2 = m_1 - (U_2 - U_1) + G(t_2 - t_1)$$

and $c_{d1}$ comprises the concentration of the urea at time $t_1$,
$c_{d2}$ comprises the concentration of the urea at time $t_2$,
$U_1$ comprises the accumulated mass of the urea at time $t_1$ and
$U_2$ comprises the accumulated mass of the urea at time $t_2$.

According to the present invention, a urea monitor is used for measuring the urea concentration $c_d$ in the effluent dialysate from a dialyzer and for determining the total removed urea (U) during the treatment. The measured values are used by a computer for estimating a pre-dialysis urea mass $m_0$ and the relative efficiency, K/V. Using these values, an indication of the dose of dialysis can be obtained on-line, for example by integrating the calculated value K/V over the treatment time. Since the pre-dialysis and post-dialysis urea masses are calculated, SRI can be determined. URR can be determined as well if the distribution volume is estimated, for example with Watson's formula, see equations (2) and (3) above. Also, equation (1) could be used since R is known. It is noted that SRI and URR are obtained as equilibrated values.

According to another approach of the present invention, it is assumed that the relative efficiency K/V is comparatively stable over at least smaller time periods and decreases continuously. If a sudden change in efficiency is determined, it could be an indication of an error condition possibly requiring nurse intervention, such as clotting of the dialyzer, or a change of blood flow $Q_b$.

According to still another approach of the present invention, the effective clearance of the dialyzer is determined by introducing a disturbance into the dialyzer and analyzing the effluent dialysate from the dialyzer in view of the disturbance. The disturbance can be an alteration of the conductivity of the dialysis fluid. By analysis of the results, it is possible to determine the effective clearance of the dialyzer. By combining the dialysate concentration of urea and the effective clearance of the dialyzer, the blood concentration of urea can be determined without the need for any invasion. By combination with the amount of urea obtained by the present invention, the distribution volume of urea can be estimated.

The measured concentration values of urea in the effluent dialysate solution has a scattered appearance, for many reasons. However, by using a special curve adaptation algorithm, it is possible to evaluate the relative efficiency, K/V, over periods where it is relatively constant in order to accurately determine relevant dialysis parameters.

BRIEF DESCRIPTION OF THE DRAWINGS

The present invention may be more fully appreciated with reference to the following detailed description, which, in turn, refers to the drawings in which.

DETAILED DESCRIPTION

The present invention is intended to be used to estimate parameters for a dialysis treatment, such as hemodialysis, hemodiafiltration or hemofiltration. It can also be used for some types of peritoneal dialysis. However, the present invention is not limited to the above-mentioned treatment modes, but can also be used for non-medical purposes.

Figure 1:
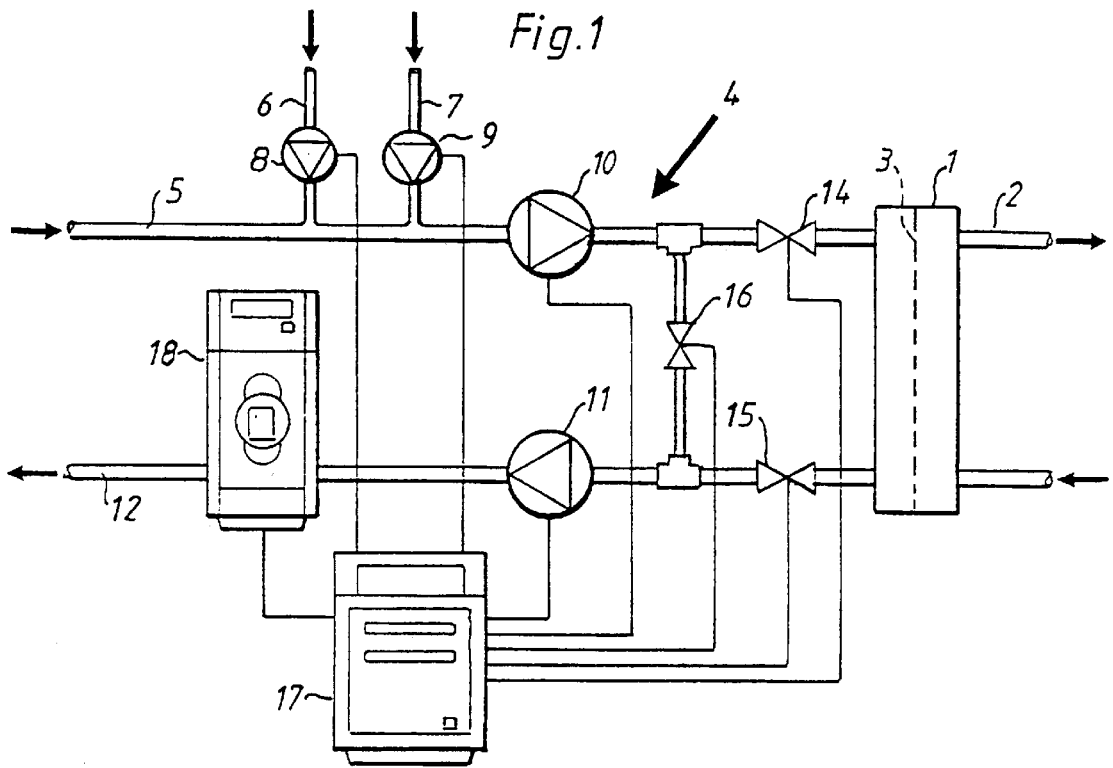
FIG. 1 is a schematic view of a dialysis machine intended for use in hemodialysis including a urea monitor in which the invention can be used.

FIG. 1 is a schematic diagram of a dialysis machine with which the present invention can be practised. The dialysis machine provides means for replacing the renal function of a mammal if the renal function is impaired or completely absent.

The blood from a patient is removed into an extracorporeal circuit 2 including a filter or dialyzer 1, including a semi-permeable membrane 3. The blood passes on one side of the membrane. On the other side of the membrane, a dialysis fluid is circulated by the dialysis machine 4.

The dialysis fluid is usually prepared by the machine from one or more concentrates and water to form a dialysis fluid having the desired properties. Thus, the machine disclosed in FIG. 1 comprises a water inlet 5, two concentrate inlets 6 and 7, and two concentrate metering pumps, 8 and 9. A first main pump 10 propels the prepared dialysis fluid to the dialysis side of the dialyzer into contact with the membrane.

A second main pump 11 passes the effluent fluid from the dialyzer, the inlet dialysis fluid and any ultrafiltrate removed from the blood through the filter, further on to an outlet 12 and to the drain.

A by-pass line 13 is arranged between the first pump 10 and the second pump 11. Several valves, 14, 15, and 16, are arranged for controlling the flow of dialysis fluid. The valves and the pumps are controlled by a computer 17 as schematically shown by several lines in FIG. 1. Of course, the dialysis machine is provided with several other means, as is conventional. These other means are not disclosed, since they are not relevant for the operation of the present invention.

The first main pump 10 is driven at a speed such that the dialysis fluid delivered to the dialyzer is substantially constant, e.g., about 500 ml/min. The second main pump 11 is driven with a slightly higher speed so that the effluent fluid, called the dialysate, has a flow rate of e.g., about 515 ml/min. This operation generates a pressure at the dialysate side of the dialyzer, which is suitable for removing about 15 ml/min of ultrafiltrate fluid from the blood, i.e. plasma water. During a treatment period of 4 hours, such ultrafiltration means a fluid removal from the patient of about 3.6 liters. Of course, the dialysis machine is operated so that the treatment prescribed for the patient is fulfilled.

In the effluent line from the dialysis machine there is a urea monitor 18, which measures the urea concentration $c_d$ in the effluent dialysate. The monitor can be positioned either inside the dialysis machine or completely outside the dialysis machine. The urea monitor can be of the type disclosed in International Application No. WO 96/04401. It is noted that this urea monitor has a conductivity sensor, so the conductivity of the dialysate is determined by the urea monitor and the urea concentration is calculated using such conductivity measurements.

The urea monitor is shown connected to the computer 17 of the dialysis machine. However, the monitor can have a computer of its own.

The urea sensor or the dialysis machine also includes means for measuring the flow rate of the effluent dialysate, $Q_d$. The computer 17 is arranged to provide concentration values $c_d$ as well as values of the total mass of urea, U, removed during the treatment as the integral of $Q_d \cdot c_d$. The concentration values are taken continuously so that a concentration curve, $c_d$, can be obtained from the urea sensor as well as a mass curve, U.

Figure 2:
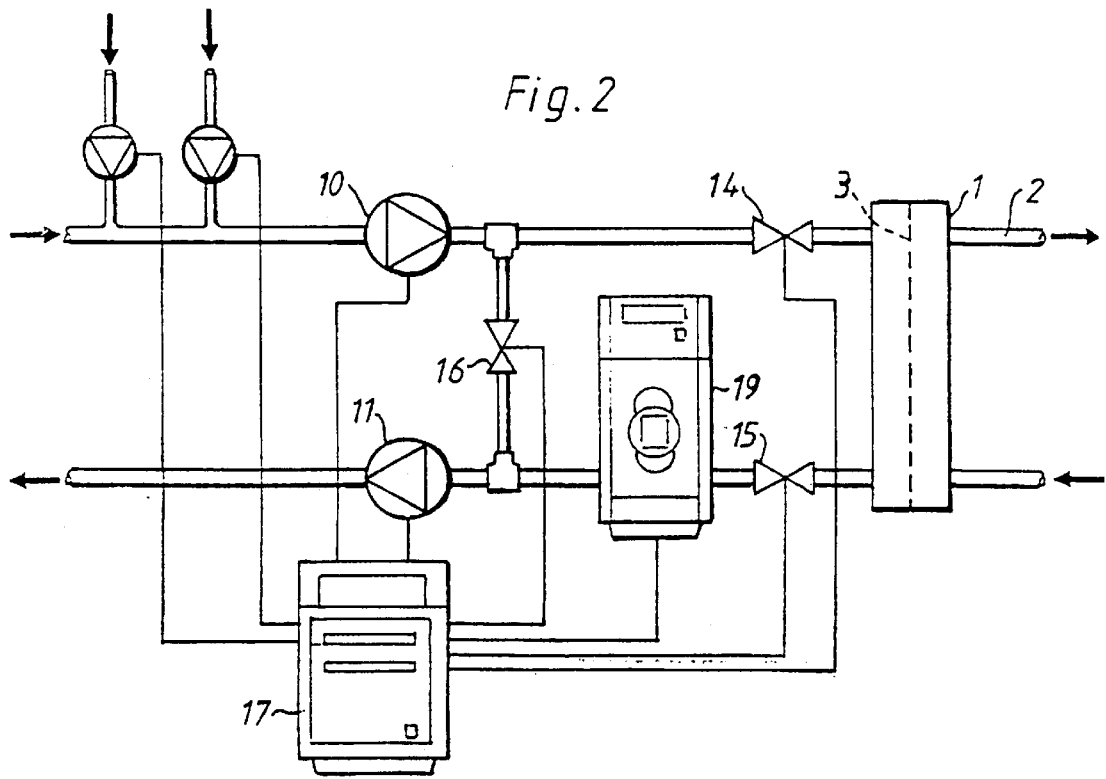
FIG. 2 is a schematic view similar to FIG. 1, but with the urea monitor integrated in the dialysis machine.

FIG. 2 discloses a similar dialysis machine to that of FIG. 1. The main difference is that in this case the urea monitor 19 is placed between the dialyzer 1 and the second main pump 11 and before the outlet of the bypass line.

Figure 3:
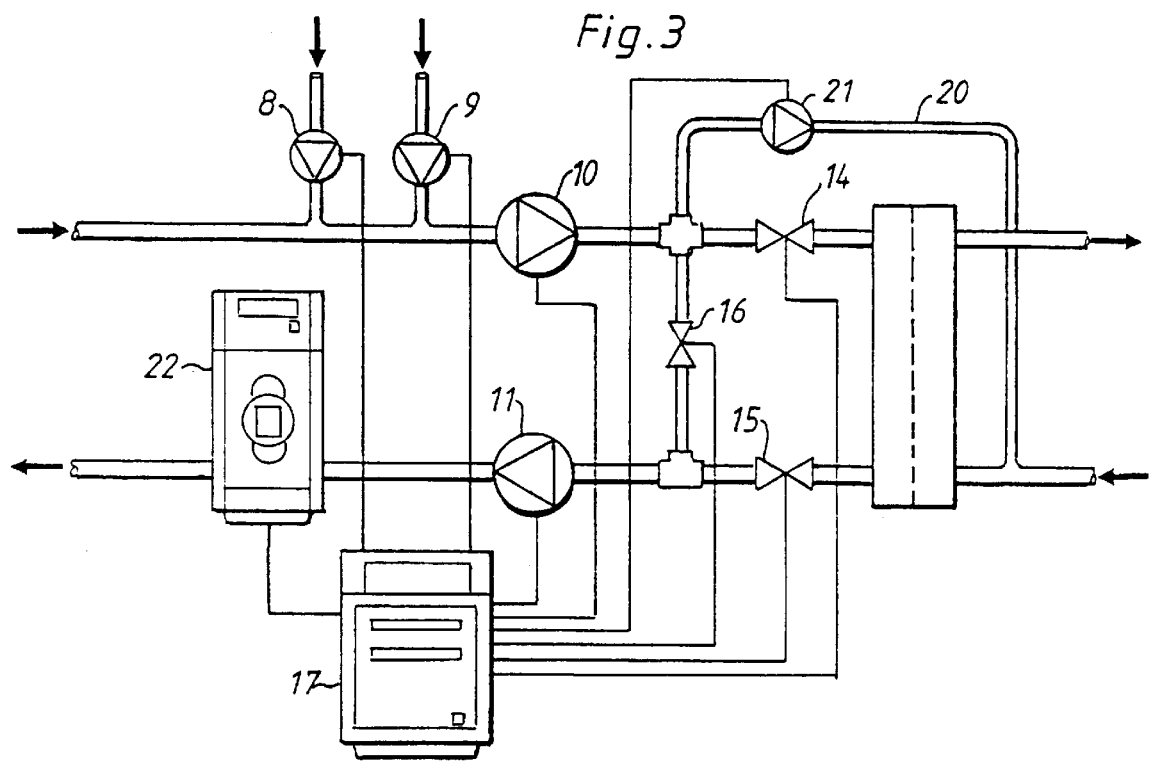
FIG. 3 is a schematic view similar to FIG. 1 of a dialysis machine adapted for use in hemofiltration.

FIG. 3 discloses a similar dialysis machine to that of FIG. 1, but in this case adapted for hemofiltration or hemodiafiltration. The only difference is that in this case there is included an infusion line 20 including an infusion pump 21. The infusion line 20 starts from the outlet of the first main pump 10 and ends at the blood inlet side of the dialyzer, for providing an infusion fluid to the blood upstream of the dialyzer, called preinfusion. The urea monitor 22 is arranged in the effluent dialysate line downstream of the second pump 11.

Figure 4:
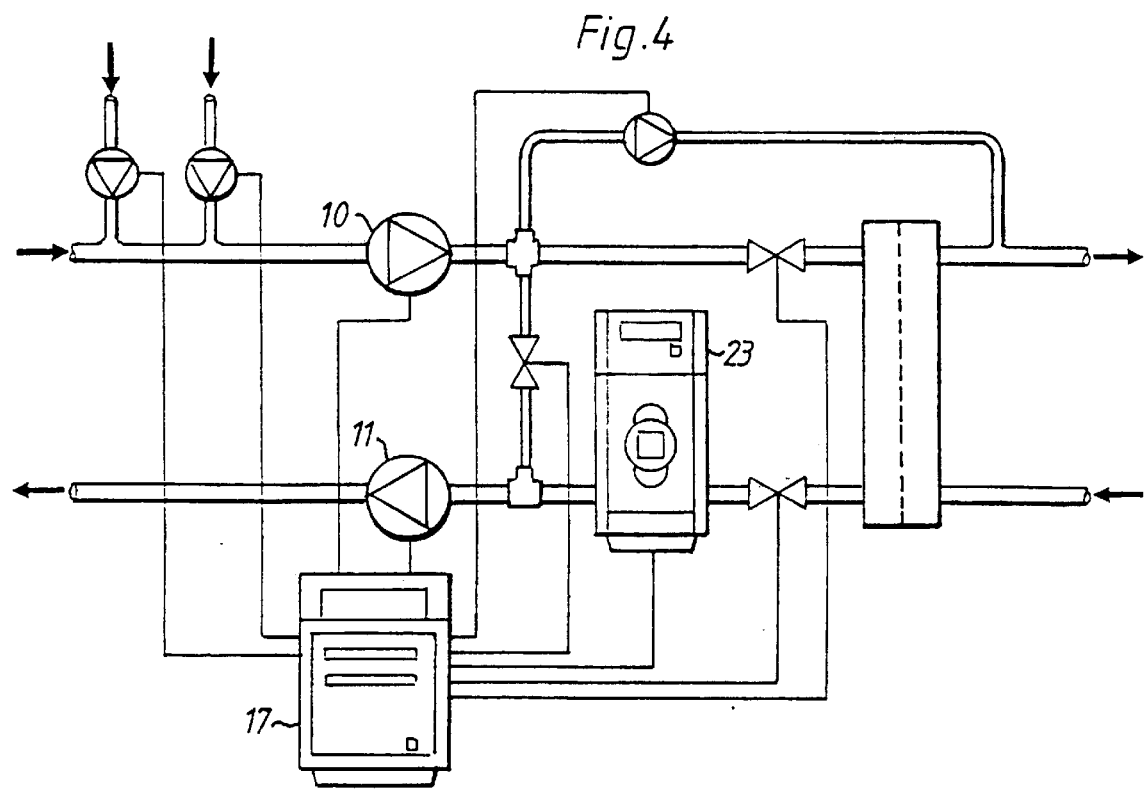
FIG. 4 is a schematic view similar to FIG. 2 of a dialysis machine adapted for use in hemofiltration.

Finally, FIG. 4 discloses a similar dialysis machine to that of FIG. 2, but in this case adapted for hemofiltration or hemodiafiltration and providing an infusion fluid to the blood downstream of the dialyzer, called postinfusion. The urea monitor 23 is placed before the second main pump 11 and before the outlet of the bypass line.

Figure 5:
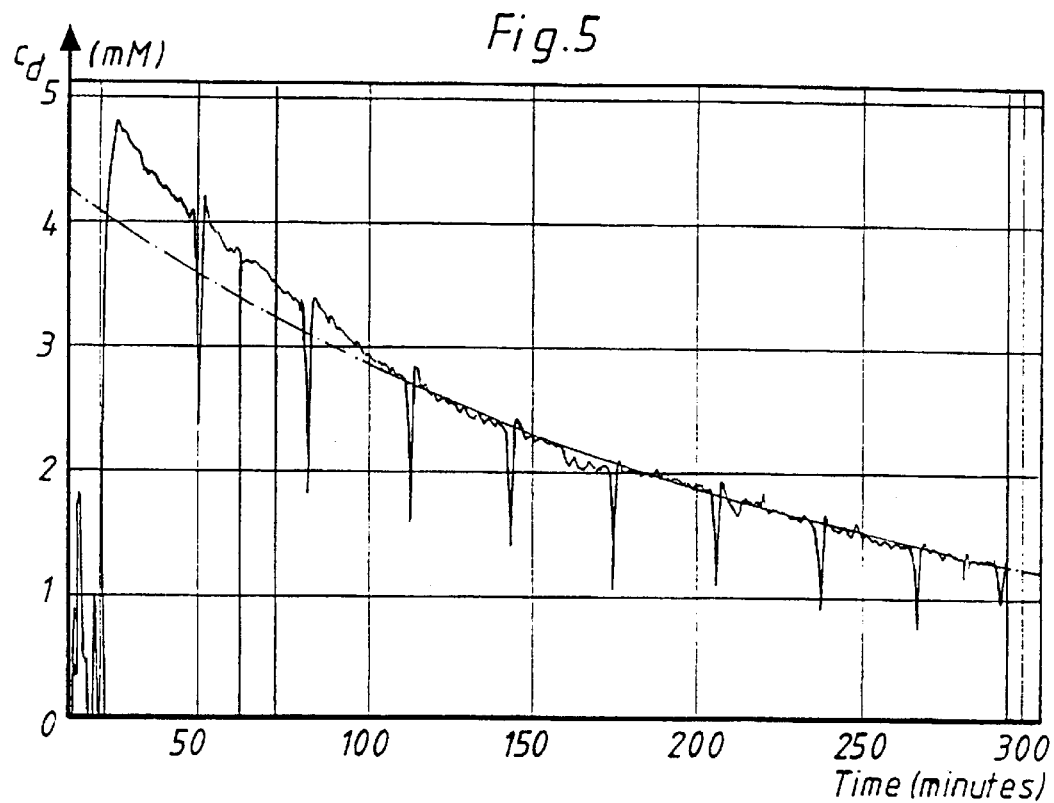
FIG. 5 is a diagram of concentration values over time obtained from the urea monitor in the dialysis machine according to any one of FIGS. 1–4.

FIG. 5 discloses a typical urea concentration curve, $c_d$, obtained from the urea sensor. As appears from this figure, the curve is very irregular and includes several dips. These dips are obtained when the dialysis machine is connected for self-calibration, when valve 16 is opened and valves 14 and 15 are closed.

Figure 6:
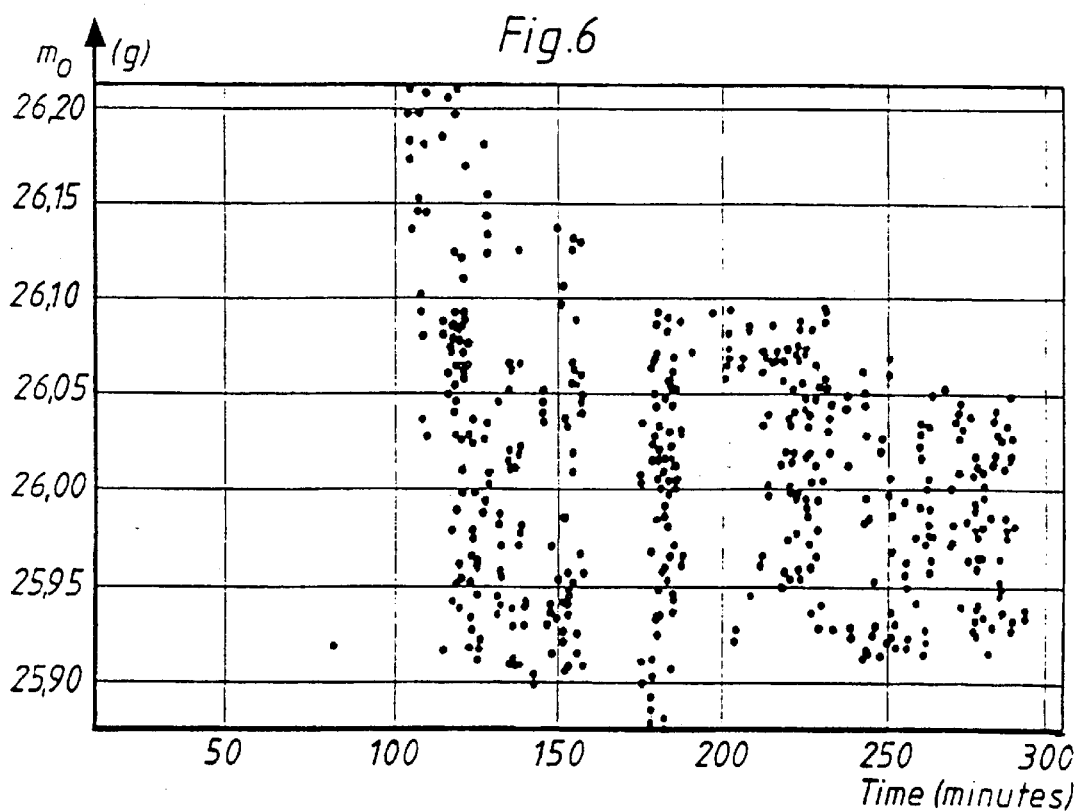
FIG. 6 is a diagram of an estimate of initial urea mass in the diagram according to FIG. 5.

FIG. 6 is a plot of urea mass values calculated according to the method disclosed in further details below.

Figure 7:
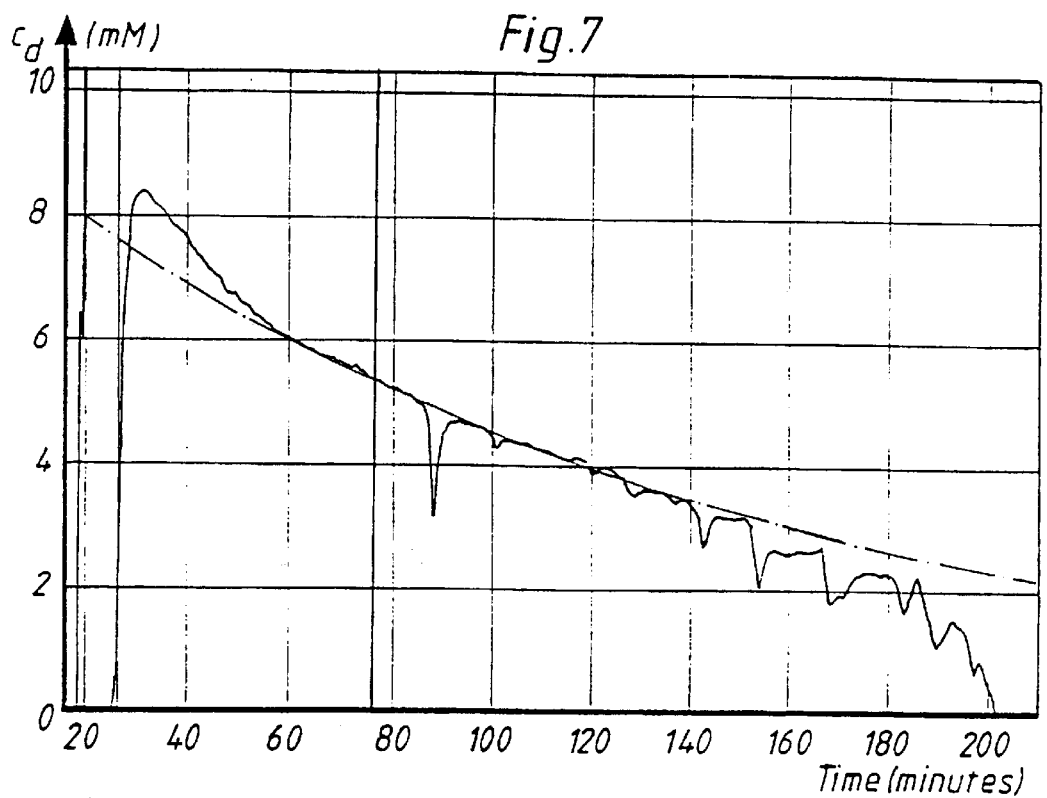
FIG. 7 is a diagram similar to FIG. 5, but showing a dialysis treatment having a problematic portion.

FIG. 7 is a concentration curve obtained during a treatment having some problematic portions, as also described further below.

Figure 8:
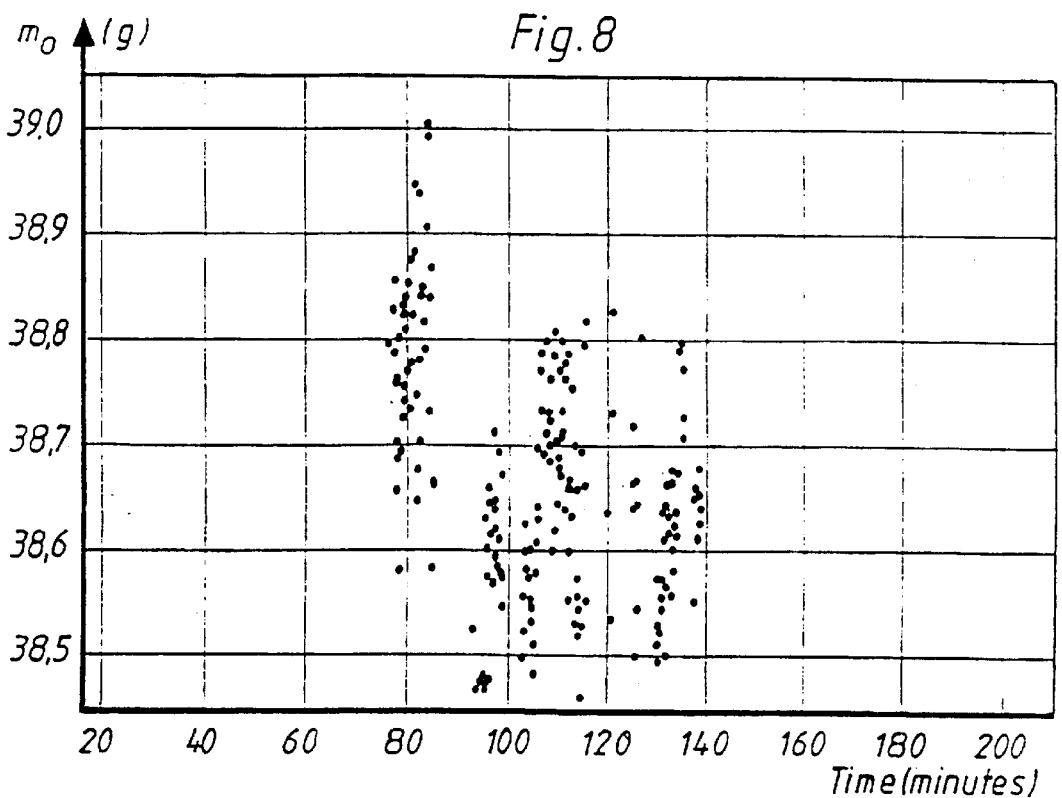
FIG. 8 is a diagram of an estimate of the initial urea mass in the diagram according to FIG. 7.

Finally, FIG. 8 is a plot of urea mass values calculated according to the method disclosed below.

There are several approaches to urea kinetics. One common approach is based on the assumption that urea is distributed in a single body compartment, namely the single pool model. It is well known that the measured urea concentration during treatments does not follow such a model, specially at high efficiency treatments.

Another approach assumes that the urea is distributed in two distinct series connected body pools with a diffusive exchange of urea therebetween. This model can explain the noted rebound after treatment, and the more rapid removal of urea at the beginning of the treatment.

Still another approach assumes that the body is divided into several compartments communicating with the blood with different time delays.

In the present invention, a urea monitor is used to measure urea concentration in the effluent dialysate from a dialyzer. Moreover, the total amount of effluent dialysate is measured. Thus, it is possible to determine the urea concentration, $c_d$, times the total dialysate flow, $Q_d$. By integrating the product of $c_d \cdot Q_d$, the total removed urea, U, is obtained.

If it is assumed that there is no accumulation of urea in the body, the total amount of removed urea (U) must be equal to urea generated (G) in the body over a certain time period, for example averaged over one week. This can be used for calculating the nutrition status or protein catabolic rate (PCR).

According to the present invention, the urea concentration measured by a urea monitor in the effluent dialysate solution from the dialyzer, is used for determining parameters of the dialysis as it progresses. These parameters are used for assessing the dialysis treatment on-line to determine the efficiency, the delivered dose, pre and post total urea masses in the body, the urea generation rate, the volume of distribution of urea in the body (for example by taking a blood sample for determining the urea concentration in the blood), and still further parameters and variables as will become evident in the description to follow.

These estimations according to the present invention are independent of any assumptions about the distribution of urea in the body.

Thus, the present invention starts from the fact that no assumption should be made about the urea distribution in the body. Instead, the total amount of urea (m) in the body at each moment is considered. According to the present invention, the definition of mean urea concentration is the mean concentration of urea in the body over a distribution volume (V).

Neither the distribution volume, nor the mean urea concentration can be measured, but we can use them for calculations. They can, however, be measured indirectly through the urea concentration measured in the effluent dialysate by the urea monitor as explained below.

Moreover, according to the present invention, the normally used dialyzer clearance is replaced by a whole body clearance K defined as the ratio between urea mass removal rate and mean urea concentration, $c_m$, in the body. The urea mass removal rate is measured by the urea monitor and is the urea concentration ($c_d$) in the effluent dialysate times the effluent dialysate flow ($Q_d$). Consequently, these definitions are:

$$K = Q_d \cdot c_d / c_m \quad (4)$$

$$m = c_m \cdot V \quad (5)$$

Since the rate of change of the urea mass in the body is the urea generation rate (G) minus the urea mass removal rate, $Q_d \cdot c_d$, the following equation is valid:

$$dm/dt = G - Q_d \cdot c_d = G - m \cdot K/V \quad (6)$$

This is a first order differential equation with time-varying coefficients which can be solved by standard methods. If we presume that K and G are constant and that V is a linear function of t ($V = V_0 - UF \cdot t$), we find that:

$$\int_0^T \frac{K}{V} ds = \ln\left[\frac{m_0 - \frac{G \cdot V_0}{K - UF}}{m_T - \frac{G \cdot V_T}{K - UF}}\right] \quad (7)$$

$$= -\ln\left[1 - \frac{m_0 - m_T G \cdot T \cdot \frac{UF}{K - UF}}{m_0 - \frac{G \cdot V_0}{K - UF}}\right]$$

$$= -\ln\left[1 - \frac{U - G \cdot T \cdot \frac{KT/V_0}{KT/V_0 - \Delta W/V_0}}{m_0 - \frac{G \cdot T}{KT/V_0 - \Delta W/V_0}}\right]$$

The assumption made for arriving at equation (7) is that the whole body clearance K is constant throughout the treatment.

Alternatively, it can be assumed that the relative efficiency K/V is constant, which results in a similar equation:

$$\int_0^T \frac{K}{V} ds = \ln\left[\frac{m_0 - \frac{G \cdot V_0}{K}}{m_T - \frac{G \cdot V_T}{K}}\right] \quad (8)$$

However, we have found that K and K/V, respectively, are not constant throughout the complete treatment, but are usually larger during an initial period of the treatment during the first 30 to 60 minutes, and are then approximately constant.

Moreover, equations (7) and (8) require the initial amount of urea, $m_0$, which must be measured prior to the dialysis treatment, for example by a blood sample or by equilibrated dialysate as described in International Application No. WO 94/08641, and by estimating the distribution volume of urea in the body.

However, the need for taking an equilibrated blood sample about 30 to 60 minutes after the treatment has been eliminated since the equation calculates the accumulated Kt/V continuously so that the treatment can be terminated when the desired dose has been achieved.

Another object of the present invention is to take a further step in using the data obtained from the urea monitor to obtain all data needed for estimating important parameters of the complete treatment. By using the idea of whole body urea mass and whole body clearance, K, it is possible to develop equations which are independent of any assumption about constant clearance, K, or constant relative efficiency, K/V, over the complete treatment period.

By combining equations (4) and (5), and by integrating the left portion of equation (6) we obtain:

$$m = (Q_d \cdot c_d)/(K/V) \quad (9)$$

and $$m = m_o + G \cdot t - U \quad (10)$$

where

G = urea generation which is assumed constant
U = total removed urea, which is equal to the integral of $Q_d \cdot c_d$ obtained from the urea monitor.

By rearranging we obtain:

$$K/V = (Q_d \cdot c_d)/(m_o + G \cdot t - U) \quad (11)$$

or $$m_o + G \cdot t = U + (Q_d \cdot c_d)/(K/V) \quad (12)$$

Equations (11) and (12) are independent of any assumptions of the urea distribution in the body or any assumption of constant K. The only assumption made is that G is constant. However, if G is not constant, the product G·t should be replaced by the integral of G over t.

Equation (11) can be used to evaluate the time dependence of K/V, which can be used for some purpose to be explained in more details below.

Like the case with equations (7) and (8), it is necessary to obtain the initial amount of urea $m_0$ in the distribution volume V of the body for equations (11) and (12).

It is possible to obtain that value by taking a blood sample before initiation of the dialysis and by estimating the distribution volume, for example by using Watson's formula.

Another method is to allow the dialysate to equilibrate with the blood at initiation of the dialysis treatment and measure the dialysate concentration, whereby the dialysate concentration equals the blood water concentration. By estimating the distribution volume, for example by Watson's formula, the initial mass of urea, $m_0$, can be obtained.

By these methods, it is possible to obtain a value of the initial mass, $m_0$, of urea, which can be used in equation (11) for obtaining the momentary relative efficiency, K/V. By integrating K/V over time, an estimate of the delivered dose, Kt/V, is obtained.

On the average, Watson's formula gives a good estimate of the distribution volume for a population of patients. However, the error for a specific patient may be large and difficult to predict. This may result in a large error in the estimate of initial mass, $m_0$.

On the other hand, and according to the present invention, it has now been found that the initial mass, $m_0$, can be calculated by using only the data obtained from a urea monitor, which measures the urea concentration, $c_d$, in the effluent dialysate from a dialyzer and the flow of dialysate, $Q_d$.

We can see that the left portion of equation (12) is a straight line with the slope G. The variables $c_d$ and $Q_d$ as well as U ($dU/dt = Q_d \cdot c_d$) are measured by the urea monitor. If we know K/V in at least two points, it is possible to calculate the constants $m_0$ and G.

It is also possible to determine G from the total removed urea during one week, which should be equal to the generation if steady state is presumed, i.e. the generation equals the removal. If the patient is dialysed three times per week, the removed urea during one such dialysis treatment can be used for estimating the generation, as disclosed by Garred et al.

If the constant $m_0$ is calculated from several measured values, it is possible to obtain a more accurate value of $m_0$ by taking the mean value or median value or other statistical value from all calculated values of the constant $m_0$.

In order to continue further, it is necessary to make an assumption about the time dependence of K/V.

Firstly, it is assumed that the instantaneous relative efficiency K/V is constant over at least some time period during the treatment. The dialysis curves obtained seem to validate the fact that there should be at least some periods with constant K/V, at least in dialysis with low ultrafiltration UF. It can be assumed that V is a linear function of time with constant ultrafiltration. However, it seems that the clearance K also varies with time in a similar manner, at least over certain time periods.

Taking the derivative of equation (12) with constant K/V we obtain:

$$G = dU/dt + Q_d \cdot (V/K) \cdot dc_d/dt \quad (13)$$

By inserting $dU/dt = Q_d \cdot c_d$ we obtain:

$$\frac{dc_d}{dt} + \frac{K}{V} c_d = \frac{G}{Q_d} \cdot \frac{K}{V} \quad (14)$$

By integrating and taking the logarithm of equation (14) we obtain:

$$\ln(c_d - G/Q_d) = \ln(c_0 - G/Q_d) - Kt/V \quad (15)$$

The curve of equation (15) is a straight line with the slope K/V. As appears from equation (15), the dialysate concentration value, $c_d$, has to be reduced by an offset term $G/Q_d$ related to the generation.

Thus, by using equation (15) in a period where the slope of the curve is constant, the momentary relative efficiency K/V can be determined in a number of points. Thus, by using equation (12), $m_0$ can be calculated for each point and an averaged (mean or median) value of $m_0$ can be estimated.

Secondly, it is assumed that K is constant over at least some time period during the treatment. The dialysis curves obtained seem to validate the fact that there should be at least some periods with constant K. We also presume that during said time period the distribution volume of urea in the body V is a linear function of time t with a constant ultrafiltration UF:

$$V = V_0 - UF \cdot t \quad (16)$$

By taking the derivative of equation (12) we obtain:

$$G = dU/dt + (Q_d \cdot V/K) dc_d/dt - (Qd \cdot c_d/K) \cdot dV/dt \quad (17)$$

which results in:

$$dc_d/dt + c_d \cdot (K - UF)/V = (K/V) \cdot G/Q_d \quad (18)$$

Equation (18) can be solved as follows:

$$c_d(t) - \frac{G}{Q_d(1 - UF/K)} = \left\{c_d(0) - \frac{G}{Q_d(1 - UF/K)}\right\} \cdot \left(\frac{V}{V_0}\right)^{\frac{K-UF}{UF}} \quad (19)$$

The expression $G/[Q_d(1-UF/K)] = c_k$ is an offset term for the measured dialysate concentration, $c_d$, due to urea generation G. The dialysis concentration, $c_d$, will approach this offset $c_k$ asymptotically for long treatment times.

Thus:

$$\ln(c_d - c_k) = \ln(c_0 - c_k) + [(K - UF)/V_0] \cdot [(V_0/UF) \ln(V/V_0)] \quad (20)$$

where $$[(V_0/UF) \ln(V/V_0)] = (V_0/UF) \ln(1 - t \, UF/V_0) = -t \quad (21)$$

By plotting the left-hand side of equation (20) versus $[(V_0/UF)\ln(V/V_0)]$ it is possible to determine the slope $[(K-UF)/V_0]$. The ultrafiltration UF is constant and known. Thus, the relative efficiency $K/V_0$ can be determined, if $UF/V_0$ is estimated. By using equation (12), $m_0$ can be determined, if the urea generation (G) is known. Otherwise, the urea generation can be determined as the time varying component of the determined $m_0$.

The determination of $m_0$ is made only over the time period where it is found that K or K/V, respectively, are constant, i.e. where the measured data fit equations (15) or (20) well enough.

As can be seen from the enclosed diagram, FIG. 3, over a dialysate concentration curve from a typical patient, $c_d$ is very irregular due to, inter alia, bypass periods, cell-to-cell checks in the urea monitor, noise and changes in the treatment efficiency (K/V) for various reasons.

It is not easy to find a curve which is the best fit for a certain time period where K or K/V should be constant. However, the Hough transform (see, U.S. Pat. No. 3,069, 654), used for finding lines in images, is a method capable of handling such types of disturbances. The Hough transform looks for straight lines that passes through the largest number of points. Therefore, even if a large number of points are outside the line, this method can still work. It will also find several lines, if there are changes in the treatment efficiency.

According to the preferred embodiment of the present invention, the following steps are performed.

The urea generation rate, G, is estimated from patient data, for example from the amount of urea removed during a week.

A continuous measurement is performed in the effluent dialysate of urea concentration, $c_d$. At the same time, the urea concentration, $c_d$, times the dialysate flow rate, $Q_d$, is integrated to provide the total removed urea, U.

The measurement is started at time zero, which is defined as the time where the measurement of urea concentration exceeds a certain level during more than five minutes.

From time zero, the urea concentration, $c_d$, is plotted versus time, and the total removed urea, U, is calculated by integrating the urea concentration, $c_d$, times $Q_d$.

Then, there is a waiting period of, for example, about 60 minutes, where it is assumed that K or K/V may be changing.

After the waiting period, the data of the urea concentration curve is processed by subtracting the offset term $G/Q_d$ from the urea concentration, $c_d$, and plotting the logarithm of the corrected urea concentration. Then, the curve is processed for finding a portion where K/V is substantially constant, as discussed above in connection with equation (15). This is performed by using the Hough transform of finding a line which passes through the largest number of points on the logarithm of the corrected urea concentration curve. When a portion of sufficient length has been located, the slope of the curve is determined for calculating K/V.

Then, a number of measurement values of the urea concentration, $c_d$, is selected which are within a certain deviation from the line obtained by the Hough transform, for example within 1% from the line. For these points, the instantaneous mass of urea is calculated by using equation (9). Finally, these instantaneous mass values are referenced to time zero, as defined above, by using equation (10) for obtaining several calculated values of $m_0$. The median value of these calculated initial mass values are regarded as the best estimate of the initial mass, $m_0$, of the body.

Our research has shown that the estimate of the initial urea mass is very accurate. Thus, the estimate of the efficiency and dose of the treatment based on this invention are also very accurate.

When the initial urea mass, $m_0$, has been obtained, it can be used in many different ways to estimate the efficiency of the treatment.

The dose of the treatment can be calculated by using equation (11) to obtain K/V at each moment of time. Then, K/V is integrated over the time to obtain Kt/V. When the desired dose has been obtained, the dialysis treatment is terminated.

If the distribution volume, $V_0$, of urea in the body is estimated, the initial urea blood concentration, $c_{b\,pre}$, in the body can be obtained without the need for taking any blood sample by dividing the estimated mass, $m_0$, by the distribution volume, $V_0$. Since the total removed urea, U, is calculated continuously, the urea mass after the dialysis treatment is known and the post urea blood concentration, $c_{b\,post}$, can be estimated since ultrafiltration is also known. The post urea concentration is the equilibrated urea concentration, since the method according to the present invention calculates on total urea mass in the body.

Thus, URR or SRI can be calculated according to equations (2) or (3). Moreover, equation (1) can be used for estimating the dialysis dose, Kt/V.

The value obtained by determination of the initial mass, $m_0$, can be used for calculating the urea distribution volume, V, of the patient, for example after completion of the dialysis session. First, the initial urea concentration in blood, $c_{b\,pre}$, is measured before the dialysis to obtain a value of the mean urea concentration before dialysis, for example by a blood sample or equilibrated dialysate measurement. This urea concentration is equal to the "mean" urea concentration according to the present invention, since urea is initially equally distributed in the body of a patient. Then, the distribution volume, $V_{pre}$, ($V_0$) can be calculated by dividing the initial urea mass, $m_0$, as calculated according to the present invention with measured blood concentration, $c_{b\,pre}$. Finally, the ultrafiltration volume removed during the treatment is subtracted to obtain, $V_{post}$, i.e. the distribution volume of urea after the dialysis treatment. This post distribution volume $V_{post}$ should be fairly constant for a normal patient in a steady state and can be used as an additional clinical parameter.

There are many alternative methods of using the principles of this invention. For example, it is possible to use the alternative method where K is assumed constant as discussed in relation to equations (16) to (19).

Instead of using the urea concentration values which are within 1% from the Hough transform line, the line itself can be used for the calculations. Moreover, the total removed urea U curve can be approximated with one or more exponential curves using the Hough transform.

Other types of curve adaptation algorithms can be used. Thus, it is possible to use the least squares method. In that case, it is necessary to remove the data portions where the dialysis machine has made some self-calibration, etc. This can be done in an iterative manner, where a first approximation is made and all data portions outside a certain limit, such as 10%, are removed and the process is repeated.

In certain types of dialysis machines, the dialysis treatment is interrupted regularly for self-calibration of the machine. In that mode, valve 16 is opened while valves 14 and 15 are closed, see FIG. 1. Thus, the dialysis of the blood ceases after a short while when the dialysis solution inside the dialyzer has obtained equilibrium with the blood. In the urea concentration curves such self-calibration periods are visible by regular dips in the curve, see FIG. 5, where such self-calibration is carried out with 30 minute intervals. After each such self-calibration, the dialysis starts again at a slightly higher level.

In order to account for such intermittent stops in the dialysis, the time scale should be adjusted to remove a portion of the stop period, since there is obviously no dialysis at least during a portion of the stop period. We have found that the best approximation to reality is obtained if the stop period is replaced by a period of 30 seconds. This is substantially independent of the actual length of the stop period, which can be anything from 35 seconds to several minutes.

As explained above, it is possible with the present invention to obtain a value of the initial mass of urea in the body of a patient. The present invention can also be utilised in other areas, where it is of interest to know the mass of a substance or composition, such as in a beer brewery.

Substances other than urea can be monitored, such as creatinine, sodium, potassium, calcium, magnesium, bicarbonate, glucose, $\beta_2$-microglobuline, etc. It is also possible to monitor the conductivity of the plasma water or blood, or the osmolarity thereof. It is also possible to use the principles of the present invention in connection with gases, such as oxygen gas, nitrogen gas or carbon dioxide gas.

If the present invention is to be used for compositions in the body having some active mechanism interfering in the body, such as for sodium and potassium ions, such interaction should be taken into account.

For sodium and potassium and some other solutes, it is customary to include some concentration of these ions in the fresh dialysis solution and therefor it is necessary to calculate the difference between initial concentration and final concentration in the effluent dialysate from the dialyzer. One approach is to replace the concentration value, $c_d$, by the concentration difference, $c_{dout}$, minus $c_{din}$ and the mean concentration, $c_m$, by the difference between the mean concentration and the initial dialysis fluid concentration, i.e. $c_m$ minus $c_{din}$. Consequently, equation (4) at page 9 will essentially be replaced by:

$$K=Q_d \cdot (c_{dout}-c_{doin})/(c_m-c_{din}) \tag{22}$$

If the treatment has followed a standard treatment with no apparent complications, the dialysis dose can be calculated by using the initial and final dialysate urea concentrations, $c_{dpre}$ and $C_{dpost}$, and using the equation:

$$URR=1-c_{d\,post}/c_{d\,pre} \tag{23}$$

If the URR calculated using the method according to the present invention differs substantially from the URR obtained with equation (23), it is an indication of problems during the dialysis, such as clotting of the dialyzer, which otherwise could have passed undetected.

For determining the urea mass by equations (15) or (19) it is assumed that the concentration follows an exponential curve over at least a portion of the curve. Since the removed urea mass U is the integral of the concentration, $c_d$, multiplied by the dialysate flow, $Q_d$, (which is constant), it follows that U is also an exponential curve over at least a portion thereof. Consequently, it is possible to use U instead of $c_d$ for calculating the momentary relative efficiency.

Alternatively, U can be used for verifying that the calculations using the concentration $c_d$ are correct. Thus, it can be assumed that U approaches an asymptote which is:

$$Asy=m_0+G\cdot t-G/(K/V) \tag{24}$$

Since all these constants are obtained from the equations given above, it is easy to calculate U minus Asy to see if this curve is an exponential curve with the same exponent as the concentration curve. If this is not the case, there is probably some error.

According to the present invention, the initial mass of urea is determined and several clinical parameters are calculated therefrom. However, the blood concentration of urea cannot be obtained, but needs to be measured by taking a blood sample and analysing it later, or by equilibrated ultrafiltration before the dialysis treatment is started. However, it is possible to determine the effective clearance of the dialyzer with a method where a disturbance is introduced into the dialyzer and the resultant effect on the effluent dialysate is analysed.

Figure 9:
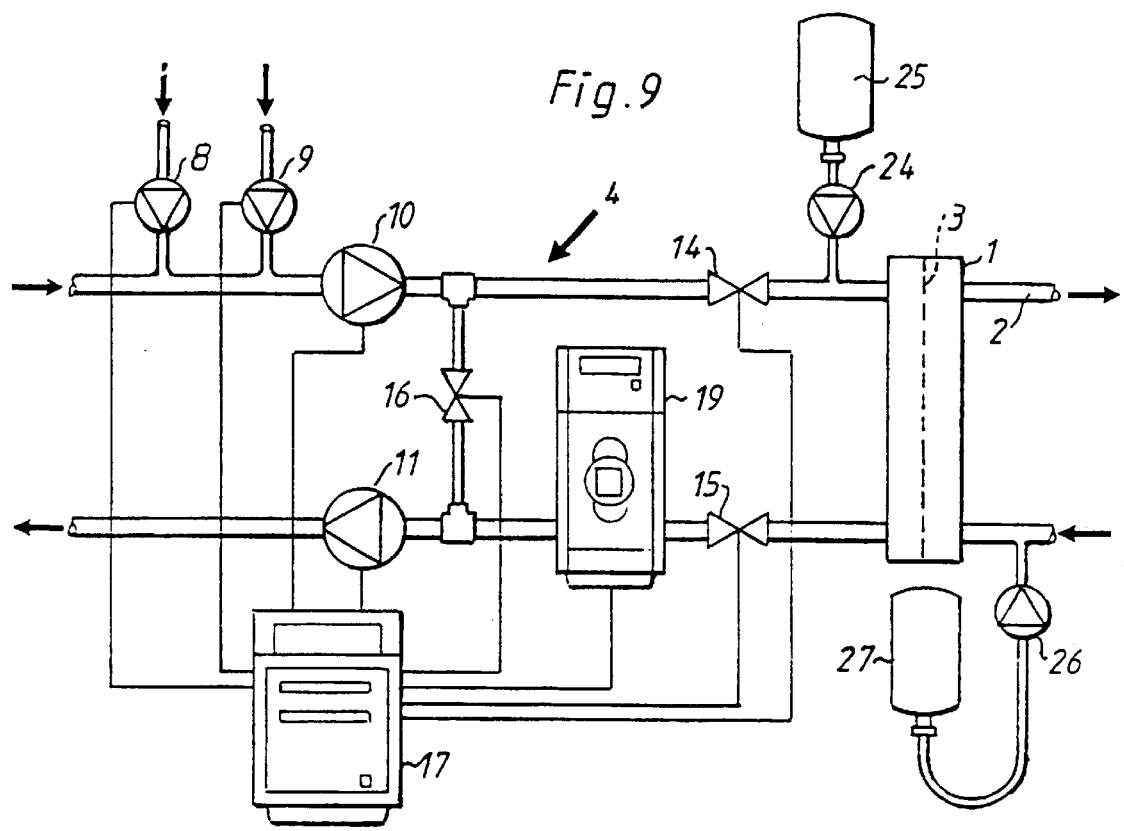
FIG. 9 is a schematic view similar to FIG. 2, including means for inducing a disturbance in the dialyzer.

Such a method is shown in FIG. 9 which is a schematic view similar to FIG. 2. In the dialysis circuit is added a pump 24 connected to the inlet of the dialyzer between the valve 14 and the dialyzer 1. To the other side of the pump 24 is connected a bag 25 comprising a material to be added to the dialysis circuit by means of pump 24.

Moreover, FIG. 9 shows a pump 26 connected to the blood circuit at the inlet of the dialyzer 1 for introducing a material comprised in a bag 27 connected to the other side of the pump 26.

Any of these devices can be used for introducing a disturbance to the inlet of the dialyzer. It is also possible to produce a disturbance by operating the concentrate pumps 8 and/or 9.

The disturbance is a change of a parameter of the dialysis fluid or the blood. The disturbance can be a change of the conductivity or a change of the urea concentration. It is noted that the urea monitor can measure both urea concentration and conductivity in the effluent dialysate. If another measurement instrument is used, any other substance can be used as a disturbance, as soon as it is compatible with the body, such as sodium, bicarbonate, etc.

The influence by the dialyzer on the disturbance is measured downstream of the dialyzer, for example by the urea sensor. A portion of the disturbing material will pass the membrane from the dialysate to the blood or vice versa. The amount passing the membrane is dependent on the dialysance of the membrane.

If the disturbance is a step change in the conductivity, produced by pumps, 8 and 9, the dialysance of the dialyzer can be determined according to equation (see European Patent No. 547,025, the contents of which is incorporated herein by reference thereto).

$$D_e = Q_d [1 - (c_{dout2} - c_{dout1})/(c_{din2} - c_{din1})] \qquad (25)$$

where $D_e$=effective dialysance of the dialyzer $Q_d$=effluent dialysate flow $c_{dout1}$ and $c_{dout2}$=concentration in the effluent dialysate $c_{din1}$ and $c_{din2}$=concentration in the introduced dialysis fluid Indexes 1 and 2 indicates before and after the step change. The introduced concentration can be measured, or it can be determined by the set values of the concentration pumps.

It is also possible to determine the effective dialysance of the dialyzer by the method disclosed in European Patent No. 658,352 where three concentrations are measured and the dialysance is determined as disclosed in that patent specification, the contents of which are incorporated herein by reference thereto.

An alternative method of determining the effective dialysance is disclosed in European Patent Application No. 97/15818, the contents of which are incorporated herein by reference thereto. The dialysance is determined by the formula:

$$D_e = Q_d \times (1 - S_{out}/S_{in}) \qquad (26)$$

where:

$D_e$=effective dialysance of the dialyzer $Q_d$=dialysate flow emitted from the dialyzer $S_{out}$=integral of Qd×(cd(t)−cd0) during the disturbance in the flow emitted from the dialyzer $S_{in}$=integral of Qd×(cd(t)−cd0) during the disturbance in the flow entered into the dialyzer The disturbance can be a change of conductivity or a change of urea concentration or any other substance that can be measured and is compatible with the body.

Figure 10:
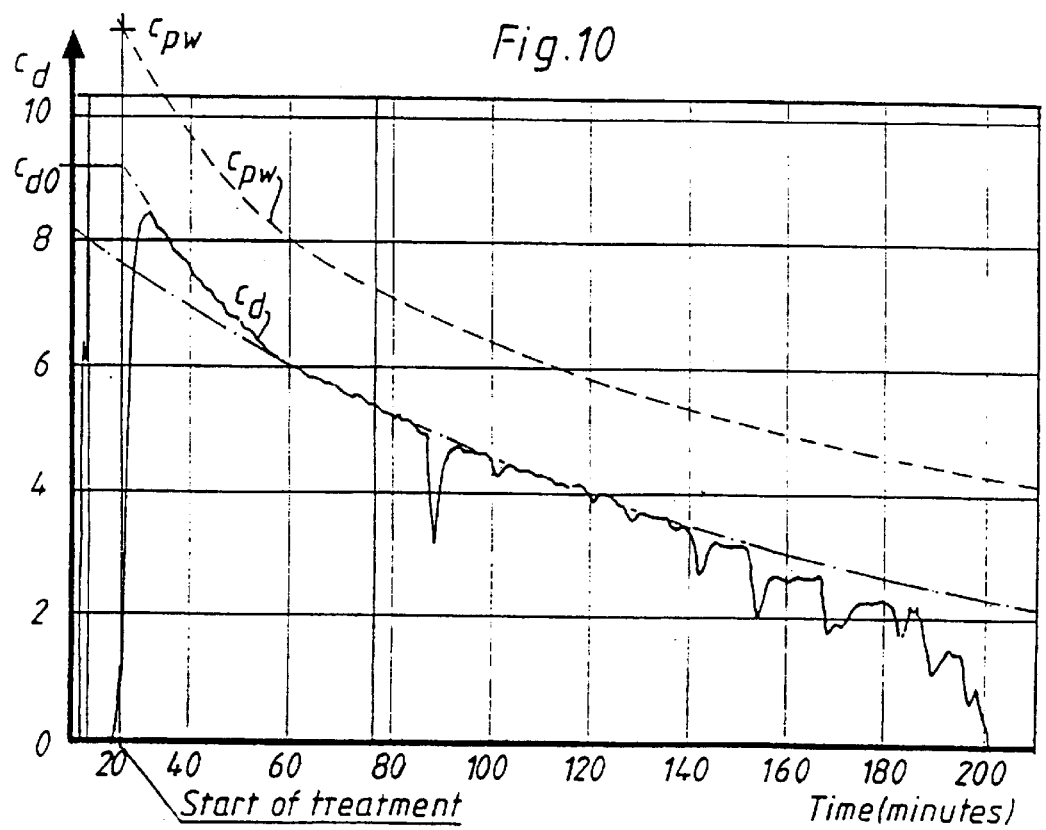
FIG. 10 is a diagram similar to FIG. 5 for determining the blood concentration of urea.

After obtaining the effective clearance of the dialyzer with any of the above-mentioned method, it is observed that the urea monitor measures the concentration of urea in the effluent fluid continuously. Thus, the urea concentration at the start of the treatment can be extrapolated from the first 5 to 20 minutes of treatment as shown in FIG. 10. Then, the plasma water concentration of urea in the body at the start of the treatment can be determined according to the formula:

$$c_{pw} = Q_d \times c_d / K_e \qquad (27)$$

where $c_{pw}$=plasma water concentration of urea at initiation of dialysis $Q_d$=effluent dialysate flow rate $c_d$=concentration of urea as extrapolated to the initiation $K_e$=effective clearance of the dialyzer for urea Since the plasma water concentration of urea can be calculated as indicated above and the amount of urea at the start of the treatment is estimated according to the present invention, the distribution volume V of urea in the body can be calculated. This distribution volume V is an important clinical parameter, which now can be measured with high accuracy.

The present invention has been described in connection with removing a substance from the body, such as urea. The same principle is valid for the addition of a substance to the body, such as bicarbonate, acetate or lactate, etc.

The present invention has been described in connection with a urea monitor, which measures the urea concentration in the dialysate continuously. It is also possible to use a measurement apparatus which measures the concentration intermittently, for example with one or a few minutes interval.

In principle, the present invention can also be used for peritoneal dialysis, where the effluent dialysate is monitored for a certain substance or composition. Specially at tidal automatic peritoneal dialysis, where the dialysate in the patient is partially replaced periodically, the principles of this invention could be applied.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for calculating a parameter of the mass exchange of a solute in a fluid comprising:

passing said solute in a predetermined volume of said fluid on one side of a semi-permeable membrane in a mass exchange device, passing an exchange fluid on the other side of said semi-permeable membrane, obtaining a solute concentration curve by repeatedly measuring the concentration of said solute in said exchange fluid, fitting an approximation curve having a logarithm comprising a substantially straight line with at least a portion of said concentration curve, determining a parameter of said approximation curve, and calculating the mass of said solute in said predetermined volume of said fluid by the formula $m=(Q_d \cdot c_d)/P$ wherein m comprises said mass of said solute, $Q_d$ comprises the flow rate of said exchange fluid, $c_d$ comprises the concentration of said solute in said exchange fluid, and P comprises said parameter.

2. The method of claim 1 including determining the flow rate of said exchange fluid, integrating the product of said flow rate of said exchange fluid and said concentration of said solute in said exchange fluid over time in order to calculate the accumulated mass of said solute in said exchange fluid, and calculating a solute reduction index by the formula:

$$SRI=(U-G \cdot t)/(m+U-G \cdot t)$$

wherein

SRI comprises said solute reduction index,

U comprises said accumulated mass of said solute in said exchange fluid,

G comprises the production of said solute over time, and t comprises time.

3. The method of claim 1 wherein said mass exchange device comprises a dialyzer, said mass exchange fluid comprises a dialysate fluid, and said solute comprises urea.

4. The method of claim 1 wherein said parameter corresponds to a whole body clearance divided by said predetermined volume of said fluid.

5. The method of claim 1 wherein said passing of said exchange fluid on said other side of said semi-permeable membrane comprises passing a finite initial concentration of said solute and wherein said measuring of said solute concentration comprises repeatedly measuring the difference of said solute concentration across said semi-permeable membrane.

6. The method of claim 1 wherein said fitting of said approximating curve comprises obtaining a compensated concentration by subtracting a predetermined concentration term from said concentration of said solute, obtaining the logarithm of said compensated concentration, and fitting a straight line to said logarithm of said compensated concentration, whereby said predetermined concentration term compensates for the generation of said solute.

7. The method of claim 1 wherein said parameter of said approximation curve comprises a slope of said substantially straight line.

8. The method of claim 1 wherein said fitting of said approximation curve excludes a predetermined initiation period.

9. The method of claim 8 wherein said predetermined initiation period comprises about 60 minutes.

10. The method of claim 1 including periodically interrupting said passing of said exchange fluid on said other side of said semi-permeable membrane for a first time period, and adjusting the time scale by replacing said first time period with a second time period, said second time period being less than said first time period.

11. The method of claim 1 wherein said parameter comprises a slope with respect to time in the following equation:

$$\ln (c_d-G/Q_d)=\ln (c_0-G/Q_d)-Kt/V \tag{I}$$

wherein $c_d$ comprises the concentration of said solute in said exchange fluid, G comprises the production of said solute over time, $c_0$ comprises the concentration of said solute in said exchange fluid at time zero, K/V comprises the relative whole body dialysis efficiency, and t comprises the time from time zero.

12. The method of claim 11 including determining the momentary mass by the equation:

$$m_1=(Q_d \cdot c_{d1})/(K/V)_1$$

wherein $(K/V)_1$ is determined in accordance with equation (I), and including determining the momentary relative efficiency at a predetermined time by the equation:

$$(K/V)_2=(Q_d \cdot c_{d2})/m_2$$

wherein $(K/V)_2$ comprises said momentary relative efficiency, $m_2$ comprises $m_1-(U_2-U_1)+G(t_2-t_1)$, $c_{d1}$ comprises the concentration of said solute in said exchange fluid at time $t_1$, $c_{d2}$ comprises said concentration of solute in said exchange fluid at time $t_2$, $U_1$ comprises the accumulated mass of said solute in said exchange fluid at time $t_1$, and $U_2$ comprises the accumulated mass of said solute in said fluid at time $t_2$.

13. The method of claim 12 including integrating said relative dialysis efficiency over time, whereby an estimate of the total dialysis dosage can be obtained.

14. The method of claim 12 wherein said fitting of said approximation curve comprises calculating a line passing through the greatest number of points in said logarithm of said concentration curve.

15. The method of claim 14 wherein said calculating is compensated.

16. The method of claim 14 including calculating said momentary mass from all values of said concentration of said solute in said exchange fluid from said substantially straight line within a predetermined time period, calculating a calculated initial mass from said momentary mass, and estimating the actual initial mass from said calculated initial mass.

17. The method of claim 16 wherein said estimating of said actual mass comprises determining the mean or median value of said calculated initial mass.

18. The method of claim 11 including determining the momentary mass of said solute in said exchange fluid by determining the actual concentration of said solute in said exchange fluid by a method selected from the group consisting of analyzing a blood sample and equilibrating said exchange fluid with blood and determining the distribution value of said solute.

19. The method of claim 1 including estimating the distribution volume of said fluid, and determining the concentration of said solute in said fluid by dividing said calculated mass by said distribution volume.

20. The method of claim 19 wherein said estimating of said distribution volume is carried out utilizing Watson's formula.

21. The method of claim 1 including measuring the concentration of said solute in said fluid and determining the distribution volume of said solute in said fluid by dividing the calculated mass and said concentration of said solute in said fluid.

22. The method of claim 3 including introducing a disturbance into said dialyzer and measuring the resulting effect in said dialysate, whereby the concentration of said solute in said fluid is measured, calculating the effective clearance of said dialyzer from said measured resulting effect on said dialysate, calculating the plasma water concentration of said solute utilizing the formula $$c_{pw} = Q_d \times c_d / K_e$$

wherein
- $c_{pw}$ comprises the plasma water concentration of urea upon initiation of said dialysis,
- $Q_d$ comprises the effluent dialysate flow rate from said dialyzer,
- $c_d$ comprises the concentration of urea extrapolated to initiation of said dialysis, and
- $K_e$ comprises the effective clearance of said dialyzer for urea; and determining the distribution volume of said urea in said fluid by means of the formula:

$$V = m_0 / c_{pw}$$

wherein $m_0$ comprises said initial mass.

23. The method of claim 1 including determining a deviation of said concentration curve from said approximation curve, and emitting an alarm based upon said deviation with respect to a predetermined threshold level.

24. The method of claim 3 wherein said parameter comprises the slope of $\ln(c_d - c_k)$ as a function of $(V_0/UF)\ln(V/V_0)$ in the equation:

$$\ln(c_d - c_k) = \ln(c_0 - c_k) + [(K - UF)/V_0] \cdot [(V_0/UF) \ln(V/V_0)] \quad (II)$$

wherein
- $c_d$ comprises the concentration of said dialysate at time t,
- $c_0$ comprises the concentration of said dialysate at time zero,
- $c_k$ comprises $G/[Q_d(1 - UF/K)]$,
- G comprises the generation of said solute,
- $Q_d$ comprises the flow rate of said dialysate,
- K comprises the whole body clearance,
- $V_0$ comprises the distribution volume prior to treatment,
- UF comprises the ultrafiltration per unit time, and
- $[(K - UF)/V_0]$ comprises said slope.

25. The method of claim 24 comprising determining said momentary mass according to the equation:

$$m_1 = (Q_d \cdot c_{d1}) / (K/V)_1$$

wherein $$(K/V)_1 = (K/V_0)/(1 - t_1 \cdot UF/V_0)$$

and $(K/V_0)$ is determined according to equation (II) and including estimating $UF/V_0$, wherein said momentary relative efficiency at a given time is determined according to the equation:

$$(K/V)_2 = (Q_d \cdot c_{d2}) / m_2$$

wherein $$m_2 = m_1 - (U_2 - U_1) + G(t_2 - t_1)$$

and
- $c_{d1}$ comprises the concentration of said dialysate at time $t_1$,
- $c_{d2}$ comprises the concentration of said dialysate at time $t_2$,
- $U_1$ comprises the accumulated mass of said solute at time $t_1$, and
- $U_2$ comprises accumulated mass of said solute at time $t_2$.

26. Apparatus for calculating a parameter of a mass exchange procedure comprising:

mass exchange means for passing a solute in a predetermined volume of a fluid on one side of a semi-permeable membrane and passing a mass exchange fluid on the other side of said semi-permeable membrane in order to exchange said mass of said solute therebetween;

measuring means for measuring the concentration of said solute in said mass exchange fluid, whereby a solute concentration curve can be provided;

first calculation means for fitting an approximation curve having a logarithm comprising a substantially straight line to at least a portion of said solute concentration curve;

second calculation means for determining a parameter of said approximation curve; and third calculation means for calculating the mass of said solute in said predetermined volume of said fluid by means of the formula $$m = (Q_d \cdot c_d)/P$$

wherein
- m comprises said mass of solute in said predetermined volume of said fluid,
- $c_d$ comprises the concentration of said solute in said mass exchange fluid,
- P comprises said parameter, and
- $Q_d$ comprises the flow rate of said mass exchange fluid.

27. The apparatus of claim 26 including flow rate determination means for determining said flow rate of said mass exchange fluid, fourth calculation means for calculating the accumulated mass of said solute in said mass exchange fluid from said mass exchange flow rate and said concentration of said solute by integrating the product of said mass exchange flow rate and said solute concentration in said mass exchange fluid over time, and fifth calculation means for calculating a solute reduction index according to the formula:

$$SRI = (U - G \cdot t)/(m + U - G \cdot t)$$

wherein
- SRI comprises said solute reduction index,
- G comprises the production of said solute over time, and
- t comprises time.

28. The apparatus of claim 27 wherein said mass exchange means comprises a dialyzer, said exchanging of said solute between the sides of said semi-permeable membrane comprises dialysis, said mass exchange fluid comprises a dialysate fluid, and said solute comprises urea.

29. The apparatus of claim 28 including flow rate measuring means for measuring the flow rate of said dialysate, and wherein said third calculation means includes means for calculating the accumulated mass of said urea in said dialysate by integrating the product of said flow rate of said dialysate and the concentration of said solute in said dialysate fluid over time.

30. The apparatus of claim 28 wherein said dialysate fluid has an initial concentration of said urea which is greater than zero, and wherein said measuring means measures the concentration difference across said semi-permeable membrane.

31. The apparatus of claim 28 wherein said first calculation means includes means for subtracting a first compensation term comprising $G/Q_d$ from said concentration of said urea in order to obtain a compensated concentration, whereby a straight line can be fitted to the logarithm of said compensated concentration so that said compensation term compensates for the production of said urea over time.

32. The apparatus of claim 21 wherein said parameter comprises the slope of said substantially straight line.

33. The apparatus of claim 21 wherein said first calculation means includes means for excluding data obtained during said initiation period.

34. The apparatus of claim 33 wherein said initiation period comprises about 60 minutes.

35. The apparatus of claim 28 wherein said first calculation means includes means for adjusting the time scale whereby when said flow of said dialysate fluid is interrupted for a first time period said first time period can be replaced with a second time period, said second time period being shorter than said first time period.

36. The apparatus of claim 28 wherein said parameter comprises the slope with respect to time, and wherein said second calculation means includes means for calculating said parameter by means of the following equation:

$$\ln(c_d - G/Q_d) = \ln(c_0 - G/Q_d) - Kt/V \quad (I)$$

wherein $c_d$ comprises the concentration of said dialysate at time t,

G comprises the generation of said urea, $Q_d$ comprises the flow of said dialysate fluid, $c_0$ comprises the concentration of said dialysate fluid at time zero, K/V comprises the relative dialysis efficiency, and t comprises the time from time zero.

37. The apparatus of claim 36 wherein said second calculation means includes means for calculating a momentary mass according to the equation:

$$m_1 = (Q_d \cdot c_{d1})/(K/V)_1$$

wherein $m_1$ comprises said momentary mass, $(K/V)_1$ is determined according to equation (I), and the momentary relative efficiency at any time is determined according to the equation:

$$(K/V)_2 = (Q_d \cdot c_{d2})/m_2$$

wherein $(K/V)_2$ comprises said momentary relative efficiency, $$m_2 = m_1 - (U_2 - U_1) + G(t_2 - t_1),$$

$c_{d1}$ comprises the concentration of said dialysate fluid at time $t_1$, $c_{d2}$ comprises the concentration of said dialysate fluid at time $t_2$, $U_1$ comprises the accumulated mass of said dialysate fluid at time $t_1$, and $U_2$ comprises the accumulated mass of dialysate fluid at time $t_2$.

38. The apparatus of claim 37 wherein said second calculation means comprises means for integrating said relative dialysis efficiency over time whereby an estimate of the total dialysis dose is provided.

39. The apparatus of claim 26 wherein said second calculation means comprises means for fitting said approximation curve by calculating a line passing through the greatest number of points in the logarithm of said concentration curve.

40. The apparatus of claim 39 wherein said calculation means includes means for calculating the momentary mass of said solute using the values of said concentration of said solute in said mass exchange fluid within a predetermined limit from said substantially straight line which can then be used to calculate the initial mass of said solute, which can be used to estimate the actual initial mass of said solute.

41. The apparatus of claim 39 wherein said second calculation means further includes means for estimating said actual initial mass based upon the median or mean value of said initial mass.

42. The apparatus of claim 37 including means for determining a momentary mass of said solute by analyzing a blood sample or by equilibration of said dialysate with blood and determining the actual concentration of said solute and measuring the distribution volume of said solute.

43. The apparatus of claim 28 including means for estimating the distribution volume of said dialysate and for determining the concentration of said urea in said dialysate by dividing said calculated mass by said volume.

44. The apparatus of claim 43 wherein said means for estimating said distribution volume utilizes Watson's formula.

45. The apparatus of claim 28 including means for measuring the concentration of said urea in said dialysate and for determining the distribution volume by dividing said calculated mass by said concentration.

46. The apparatus of claim 28 wherein said measuring means comprises means for introducing a disturbance into said dialyzer, means for measuring the resulting effect in said dialysate and for calculating the effective clearance of said dialyzer from said resulting measurements, means for calculating the plasma water concentration of said solute by the formula:

$$c_{pw} = Q_d \cdot c_d / K_e$$

wherein $c_{pw}$ comprises the plasma water concentration of urea at the initiation of said dialysis, $Q_d$ comprises the flow rate of said dialysate, $c_d$ comprises the concentration of said urea extrapolated to said initiation of said dialysis procedure, $K_e$ comprises the effective clearance of said dialyzer for urea, and including means for determining the distribution volume V of said urea using the formula $V = m_0/c_{pw}$ where V comprises said distribution volume.

47. The apparatus of claim 28 including means for determining a deviation of said concentration curve from said approximation curve and alarm means for emitting an alarm upon deviation greater than a predetermined threshold level.

48. The apparatus of claim 28 wherein said parameter comprises a slope and wherein said second calculation means comprises means for calculating said slope in the equation:

$$\ln(c_d - c_k) = \ln(c_0 - c_k) + [(K-UF)/V_0] \cdot [(V_0/UF) \ln(V/V_0)] \quad \text{(II)}$$

wherein $[(K-UF)/V_0]$ comprises said slope of a predetermined line, $\ln(c_d - c_k)$ comprises said line, $c_d$ comprises the concentration of said dialysate at time t, $c_k$ comprises $G/[Q_d (1-UF/K)]$, G comprises the generation of said urea, $Q_d$ comprises the flow of said dialysate, $c_0$ comprises a concentration of said dialysate at time zero, K/V comprises the relative dialysis efficiency, and UF comprises the ultrafiltration over time.

49. The apparatus of claim 48 wherein said second calculation means includes means for calculating a momentary mass according to the equation:

$$m_1 = (Q_d \cdot c_{d1})/(K/V)_1$$

wherein $$(K/V)_1 = (K/V_0)/(1 - t_1 \cdot UF/V_0),$$

$(K/V_0)$ is determined according to equation (II) and $UF/V_0$ is estimated, and the momentary relative efficiency at any given predetermined time is determined according to the equation:

$$(K/V)_2 = (Q_d \cdot c_{d2})/m_2$$

where $(K/V)_2$ comprises said momentary relative efficiency, $$m_2 = m_1 - (U_2 - U_1) + G(t_2 - t_1)$$

and $c_{d1}$ comprises the concentration of said urea at time $t_1$, $c_{d2}$ comprises the concentration of said urea at time $t_2$, $U_1$ comprises the accumulated mass of said urea at time $t_1$, and $U_2$ comprises the accumulated mass of said urea at time $t_2$.

* * * * *

UNITED STATES PATENT AND TRADEMARK OFFICE
CERTIFICATE OF CORRECTION

PATENT NO. : 6,258,027 B1
DATED : July 10, 2001
INVENTOR(S) : Jan Stemby

It is certified that error appears in the above-identified patent and that said Letters Patent is hereby corrected as shown below:

Column 13,
Lines 11 and 12, in equation (7), "$G.T.\frac{UF}{K\text{-}UF}$" should read -- $\frac{G.T.UF}{K\text{-}UF}$ --

Column 15,
Line 60, "≡" should read -- ≅ --.

Column 25,
Lines 20 and 22, delete "21" and substitute therefor -- 26 --.

Signed and Sealed this

Twenty-seventh Day of May, 2003

JAMES E. ROGAN
*Director of the United States Patent and Trademark Office*